United States Patent [19]

Avakian et al.

[11] 4,372,304
[45] Feb. 8, 1983

[54] FLOW CONTROL SYSTEM AND RESTRICTOR FOR USE THEREIN

[75] Inventors: Emik A. Avakian, Springfield, Mass.; Souren Avakian, Westport, Conn.

[73] Assignee: Centaur Sciences, Inc., Stamford, Conn.

[21] Appl. No.: 197,272

[22] Filed: Oct. 15, 1980

[51] Int. Cl.³ .............................................. A61M 5/00
[52] U.S. Cl. ............................... 128/214 E; 137/486; 137/487.5; 251/8
[58] Field of Search ............................ 137/480, 487.5; 128/214 E, DIG. 13; 251/8

[56] References Cited

U.S. PATENT DOCUMENTS

| | | | |
|---|---|---|---|
| 3,450,153 | 6/1969 | Hildebrandt | 137/486 |
| 3,601,124 | 8/1971 | Petree | 128/214 E |
| 3,871,229 | 3/1975 | Fletcher | 128/214 E |
| 3,990,443 | 11/1976 | Fletcher | 137/487.5 X |
| 4,094,318 | 6/1978 | Burke | 128/DIG. 13 X |
| 4,105,028 | 8/1978 | Sadlier | 128/214 E |
| 4,146,029 | 3/1979 | Ellinwood | 128/260 |
| 4,217,993 | 8/1980 | Jess | 128/DIG. 13 X |
| 4,261,388 | 4/1981 | Shelton | 137/487.5 X |
| 4,286,590 | 9/1981 | Murase | 128/214 E |
| 4,294,248 | 10/1981 | de Figueiredo | 128/214 E |

*Primary Examiner*—Alan Cohan

[57] ABSTRACT

The rate and total quantity of a fluid being delivered intravenously to a patient are accurately controlled by a restrictor which operates under the supervision of a microprocessor. The microprocessor provides control signals to a stepping motor which, through appropriate gearing, causes movement of a plunger so as to increase or decrease the compression of a plastic tube of an IV set which is captured in a disposable adapter mounted in registration with the plunger.

22 Claims, 7 Drawing Figures

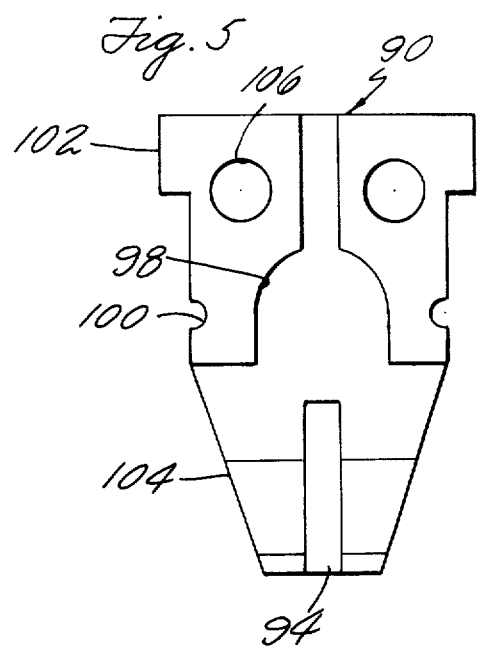
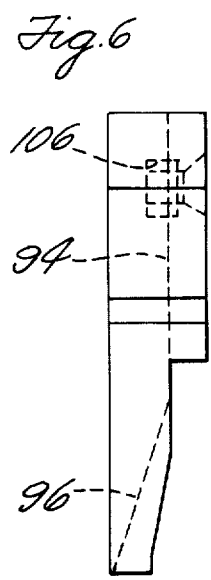
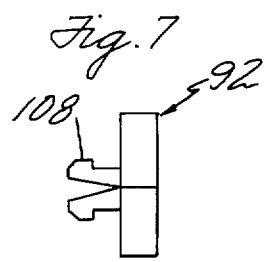

FLOW CONTROL SYSTEM AND RESTRICTOR FOR USE THEREIN

BACKGROUND OF THE INVENTION (1) Field of the Invention

The present invention relates to the precise exercise of control over the flow of liquid from a reservoir to a consuming unit and particularly to regulating fluid flow in the form of discrete drops in the intravenous application of the fluid to a patient. More specifically, the present invention is directed to a microcomputer based intravenous fluid flow control system and a restricter for use in such system. Accordingly, the general objects of the present invention are to provide novel and improved methods and apparatus of such character.

(2) Description of the Prior Art

While not limited thereto in its utility, the present invention is particularly well suited for medical applications wherein the flow rate and/or total quantity of a liquid, being fed intravenously to a patient must be precisely controlled. Such precise flow regulation should preferably be accomplished both reliably and accurately. Additionally, a control for a drop-feed intravenous system should be easy to calibrate and operate.

A number of "automatic" IV systems have been proposed in the prior art. A common characteristic of such prior systems resides in the mode of flow control. Since it is desired to employ disposable plastic tubing in an IV set, the flow control "valve" has typically been a constrictor which operates by pinching the tubing. The state of the art of exercising control over the flow rate of a liquid being delivered intravenously to a patient is believed to be exemplified by the disclosures of U.S. Pat. Nos. 3,596,515, 3,601,124 and 3,871,229. As may be seen by reference to these examples of the prior art, an intravenous flow control system will include a reservoir for the fluid to be delivered to the patient, a drop sensor which measures the rate at which the fluid exits the reservoir and a motor operated constrictor which controls the flow rate to the patient in response to an operator selected reference signal and the measured drop rate. Typically, when a difference between the selected flow rate and the drop rate are detected an error signal will be generated. This error signal is delivered to the drive motor of the constrictor and will result in the tube connected to the patient, at a point downstream of the drop sensor, either being more or less compressed to ensure that the delivery rate is maintained at the selected value.

The prior art IV systems, as exemplified by the above-listed patents, possessed certain disadvantages. Foremost among these disadvantages was a limitation on the degree of accuracy which could be achieved since analog circuit techniques were employed. Additionally, system set-up was a comparatively difficult and time-consuming endeavor.

SUMMARY OF THE INVENTION

The present invention overcomes the above-briefly discussed and other deficiencies and disadvantages of the prior art by providing a novel and improved technique for exercising precise control over the rate of flow of a liquid through a conduit and particularly for controlling the feed rate of a fluid being delivered intravenously to a patient. The present invention also contemplates an IV system for use in the practice of such method and a novel restrictor for use in such system.

Apparatus in accordance with the present invention comprises a microprocessor based flow control which employs a keyboard, through which information may be inputed, and a visual display of those parameters which may be of interest to the operator. The microprocessor provides output signals to a stepping motor which is coupled to a novel restrictor. The output of the stepping motor, through appropriate gearing, causes movement of a "plunger" in the restrictor which contacts and compresses the tubing through which the fluid flows. Apparatus in accordance with the present invention has the capability of, for example, varying the rate of delivery between 100 and 101 drops per minute through controllably retracting the "plunger" in steps of ½ micron.

The restrictor, in accordance with a preferred embodiment of the present invention, comprises a "plunger" sub-assembly and a throw-away two-piece tube-supporting adapter which is easily mated to and removed from the "plunger" sub-assembly. The tube through which the fluid flow is to be controlled is inserted in the first part of this adapter and a cap snapped thereover to maintain the tube in the adapter. The adapter is then simply slipped into position on the end of the "plunger" sub-assembly to place the system in condition for operation.

BRIEF DESCRIPTION OF THE DRAWING

The present invention may be better understood and its numerous objects and advantages will become apparent to those skilled in the art by reference to the accompanying drawing wherein like reference numerals refer to like elements in the several figures and in which:

FIG. 5 is a front view of the tube receiving adapter of the restrictor of FIGS. 3 and 4.

FIG. 6 is a side view of the adapter of FIG. 5.

FIG. 7 is a side view of the cap portion of the adapter of FIGS. 5 and 6.

DESCRIPTION OF THE PREFERRED EMBODIMENT

Figure 1:
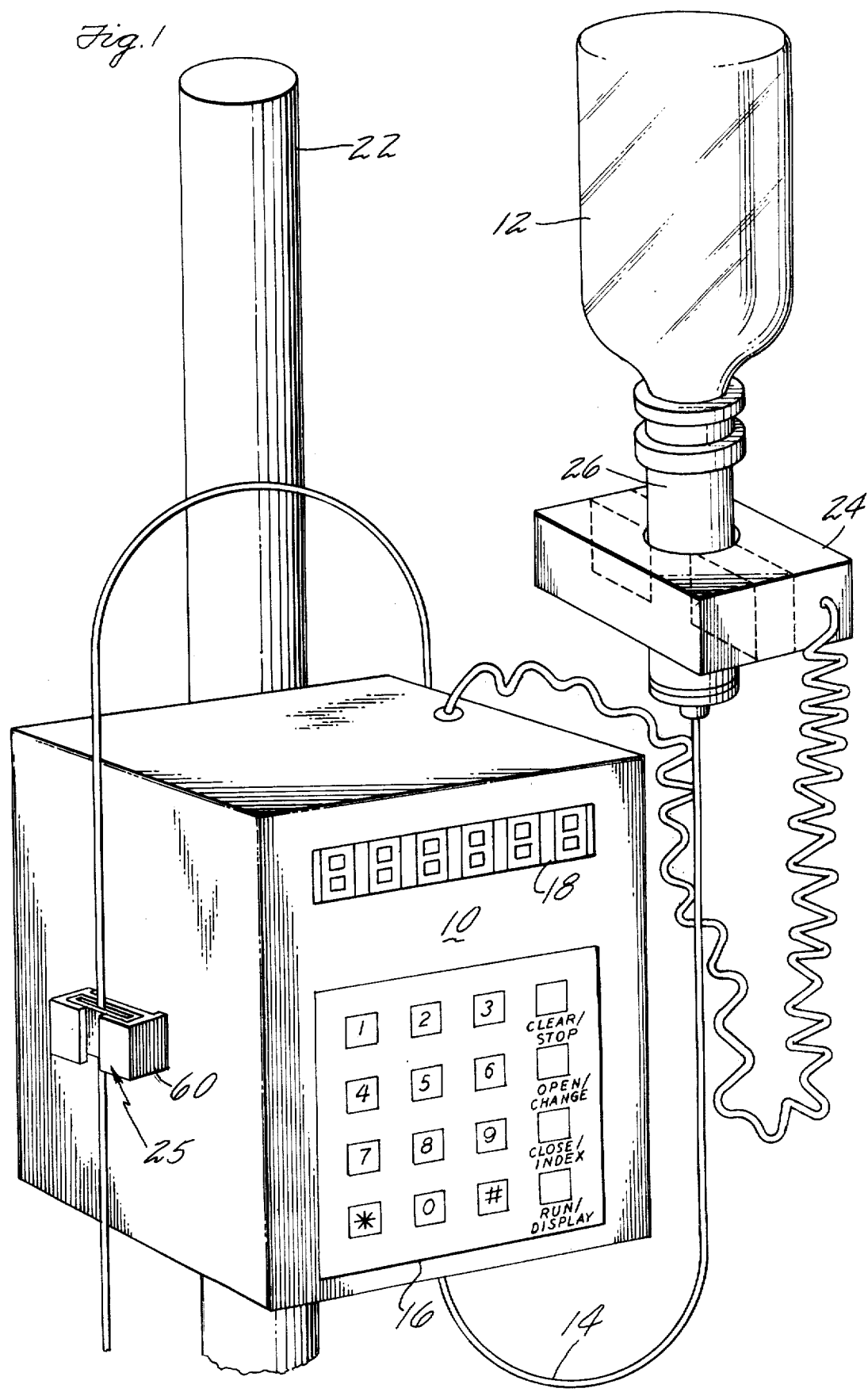
FIG. 1 is a perspective view of a microcomputer driven IV system in accordance with the present invention.

Referring now to the drawing, and particularly to FIG. 1, an IV feed system in accordance with the present invention is depicted. This IV system comprises a control, indicated generally at 10, which automatically adjusts the rate of flow of a liquid being delivered to a patient from a reservoir bottle 12 via an I.V. set which includes a flexible plastic tube 14. The control 10, as will be described in greater detail below, includes a microprocessor, a keyboard 16, a display 18, and a motor-driven plunger assembly. The end of the plunger of this assembly projects outwardly through the side panel of the housing of controller 10 and forms a part of a restrictor, indicated generally at 20, which will be described in greater detail below in the discussion of FIGS. 3-7. The tube 14 will pass through restrictor 20 as shown whereby the flow rate of liquid from reservoir 12 to the patient may be automatically and precisely regulated by the microprocessor which exercises control over the motor which drives the restrictor plunger.

The system FIG. 1, which may conveniently be mounted on a vertical post 22 as shown, also includes a drop sensor 24 which accurately counts the drops of fluid which exit reservoir 12; drop sensor 24 being associated with a drop chamber 26 in the manner known in the art. The drop sensor 24 preferably comprises a highly sensitive infrared detector but may be one of the devices of the three above-referenced prior art patents. Drop sensor 24 provides, via electrical cable 28, a first input signal to the microprocessor in controller 10. Further inputs to the microprocessor are generated by the operator through the keyboard 16 and by limit switches associated with the actuator for the restrictor plunger.

Figure 2:
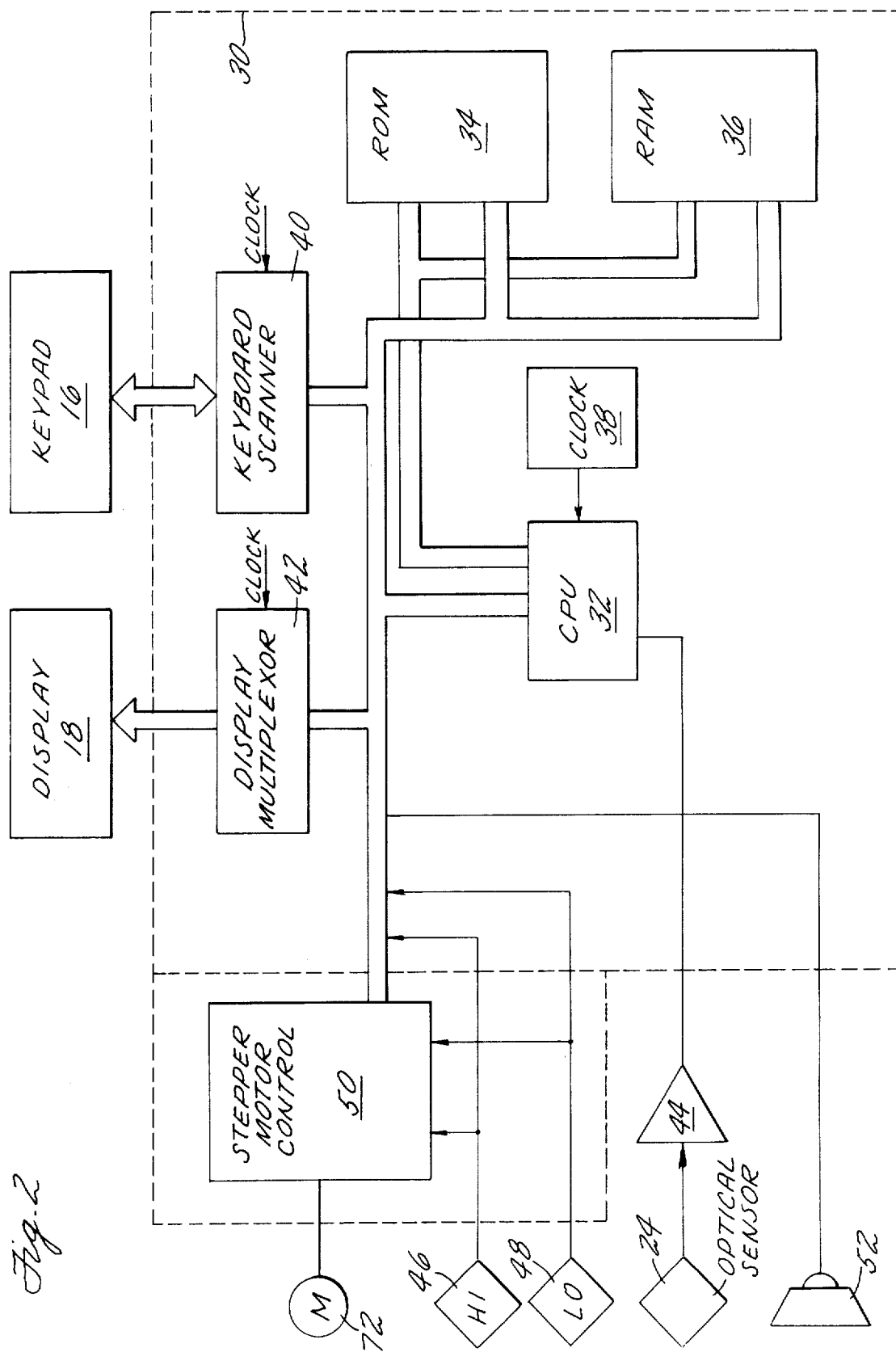
FIG. 2 is block diagram illustrating the electrical components of the system of FIG. 1.

Referring to FIG. 2, a block diagram of the controller 10 is presented. The principal element of controller 10 is a microprocessor 30 which includes a central processing unit (CPU) 32, a read only memory 34, a random access memory 36, a clock 38 and interface devices for coupling the data bus of microprocessor 30 to the keyboard 16 and display 18. These interface devices include a keyboard scanner 40 and display multiplexer 42. It is to be noted that microprocessor 30 is of conventional construction and does not per se comprise part of the present invention.

The stored program for operation of the flow control system of the present invention, which will be described below, is loaded into ROM 34. Data inputed by means of keyboard 16, as well as the results of computations performed by CPU 32 pursuant to the stored program, are entered into RAM 36 which functions as a scratch-pad memory. Microprocessor 30, in addition to receiving input data from keyboard 16, will receive the drop rate signals provided by drop sensor 24; the signals first being amplified in amplifier 44. A pair of further inputs to microprocessor 30 are provided by limit switches 46 and 48 which will be mounted so as to define the limits of excursion of the plunger of the restrictor 20. Microprocessor 30 provides information, on a data bus, for outputting to display 18 via multiplexer 42 and for delivery to a stepper motor control 50. The motor controller 50 will be a commercially available device which provides the output signals for controlling the position of the output shaft of a stepping motor 72 which drives the plunger of the restrictor. In one reduction to practice of the invention the stepping motor 72 was a bidirectional motor having 48 steps per revolution. This motor had, within its housing, a gear case providing a step down ratio of 20 to 1. Accordingly, one step of the motor produced almost one thousandths of a revolution. This arrangement, coupled with the plunger drive to be described below in the discussion of FIGS. 3 and 4, resulted in each step of the motor producing approximately 1/80,000 of an inch movement of the tube compressing plunger in a direction transverse to the axis of tube 14. A further output of microprocessor 30 is delivered as the energizing input to an audible alarm 52.

Before describing the restrictor 20 in greater detail, the operation of the system of FIGS. 1 and 2 will be discussed. In order to initiate infusion of a liquid, the operator will position the tube 14 in an adapter, which forms part of the restrictor 20, and will then mount that adapter on the side of the controller 10. This part of the set-up procedure will be described in greater detail below in the discussion of FIGS. 3-7. As part of the insertion of the tube 14 in the restrictor 20, the operator will normally depress the "Open" key on key-board 16. The pressing of the "Open" key will deliver a signal to the microprocessor which will cause the stepping motor, which is controlled by the microprocessor, to retract the restrictor plunger to the fully withdrawn position thereby allowing the adapter and tube to be placed on the controller. The drop chamber 26 will be installed on the bottle 12 and the bottle hung in the customary manner. If fluid does not flow freely through the tube 14 at this time, thus purging the set of air, the "Open" key will be again depressed. It is to be noted that the microprocessor is programmed to produce a slow rate of opening of the restrictor; i.e., a slow retraction of the motor operated plunger; as long as the "Open" key is activated. When all the air is purged from the set, the "Close " key is pushed and held in the depressed position until the fluid stops dripping. The plunger of the restrictor will be extended, thereby pinching the tube 14, as long as the "Close" key is held in the depressed position. Next, the operator will push the "Set-Up" key followed by the "Go" key. The "Go" key is employed as a second key depression of a key entry to insure against accidental keying. Sequences of two-key actions must be performed within a five second span. Any key depression requiring a sequence will be ignored by the system if the entire sequence is not performed within the five seconds. After the "Set-Up" and "Go" key sequence has been accomplished, the operator may enter a set-up index number which designates the type of set-up being used as well as the kind of liquid to be administered. It is to be noted that there are five different set-ups customarily employed by different suppliers of the various fluids which may be administered employing the present invention and there are three classes of such fluids. This results in fifteen different drop values per minute for each cc per hour to be administered. The set-up index may thus assume fifteen different values and the microprocessor will compute the volumes according to these fifteen different conversions. The system will respond to the entry of the set-up index number by displaying the number in the fifth and sixth positions; positions 1-4 being blanked. It is to be noted, however, that the operator may choose not to enter a set-up index number but rather may depress the "Go" key a second time. If the "Go" button is pushed for the second time with or without entering a set-up index, zeros will appear in positions 1-3 for the entry of the drop rate and all other digits will blank. At this point in time the operator must enter the desired drop rate. Failure to enter the drop rate will result in the apparatus ignoring further commands.

When the operator enters the drop rate and subsequently pushes the "Go" key, the drop rate will appear, as in all other entries, right to left. If only one or two digits are used, the remaining zeros will be blanked when the "Go" key is activated. Also, when the "Go" key is activated, the entered digits of the drop rate are also blanked but remain in the system. Activation of the "Go" key after entry of the drop rate will result in the three right-most digit positions displaying zeros indicative of the need to next enter the volume to be infused. It is to be noted that whenever the volume to be infused or the drop rate or both are to be displayed, there will be a dot at the lower right side of the third digit which acts as a demarcation point.

Entry of the volume to be infused consists of entering the cubic centimeters via the numerical keyes on keyboard 16 followed by activation of the "Go" key. Entry of the volume results in the numbers appearing on display 18 from left to right. If there are remaining zeros to the left of the significant numbers, they will be blank when the "Go" key is activated. When the "Go" key is depressed, the controller will seek the proper drop rate. When the proper rate is attained, the three drop rate digits reappear on display 18 to indicate that the system is ready for the infusion.

When the system indicates that infusion may begin, the patient will be connected and the "Go" key again pushed. This results in the drop rate digits again being blanked and the three volume digits being displayed. A countdown will then begin on the volume to be infused. The drop rate digits are blanked to conserve power while running and, during infusion, the volume yet to be infused will be continuously displayed. In order to actually begin infusion, however, the operator must push the "Run/Display" key and then again depress the "Go" key. This sequence of key operations changes the mode of operation of the system from set-up to run. During the run mode, as noted above, there will be a countdown of the volume to be infused digits. When all zeros are reached in this countdown, the system will go into an alarm condition wherein the original volume digits as well as the drop rate digits will be displayed and the display will flash.

It is possible, when in the run mode, to change the the flow rate and to stop and restart infusion. Similarly, during the set-up mode it is possible to clear previously entered data, to review data previously entered and to manually open or close the restrictor. The position of the plunger operated by the motor in controller 10; i.e., the degree of opening of the restrictor; cannot be manually varied with the device in the run mode. Thus, by way of example, the system will ignore an "Open" followed by a "Go" sequence in the run mode. Emergency shut off is accomplished by a sequence of activating the "Stop" key followed by the "Go" key. Applicant will not herein discuss the system response to the aforementioned changes which may be accomplished during the run and set-up modes.

The apparatus of FIGS. 1 and 2 also has the capability of displaying the elapsed infusion time. This is accomplished by depressing the "Display" key followed by activating the #1 key. If the operator wishes to know the total number of drops infused, the "Display" key is depressed followed by the #2 key. Return to the primary display; i.e., the display of the volume to be infused; is accomplished by depressing the "Display" key twice.

The system of the present invention has three separate alarm conditions. A first alarm condition is established when the drop sensor 24 does not count two drops within an expected time period as established by the drop rate set into the system. This, of course, indicates that the drop rate is too slow. The alarm is triggered by no drops being detected for a period of time which is the reciprocal of the set drop rate per minute. Thus, if the expected time between two drops is "t", the system waits for a period "dt" before automatically initiating a corrective action. The period "dt" has four different values depending on the drop rate entered by the operator. If a period "t" plus "dt" elapses between a pair of drops, pairs of pulses are delivered to the plunger drive motor every quarter of a second for a period of ten seconds. If a drop does not appear after this ten second period, an audible alarm is initiated and the display is caused to flash. If more drops are detected than would be expected in the period between drops as determined by the drop rate entered by the operator, the alarm may also be activated. After each drop is detected, the microprocessor calculates the number of drops per minute based on the time between the last two drops. Corrective action is taken if there are more than two drops during a period when there should only be one drop. The corrective action will be the generation of a number of pulses which cause the motor to extend the plunger thereby closing the restrictor. The number of pulses will be a function of the difference between the instantaneous drop rate, as computed by the microprocessor, and the drop rate entered by the operator. The third alarm condition occurs when the countdown of the volume-to-be-infused reaches zero. This third alarm condition was discussed above.

Referring to FIGS. 3–7, the novel restrictor of the preferred embodiment of the present invention will now be described. This restrictor, indicated generally at 20, functions, as a gating mechanism which receives the plastic tube 14 extending from the reservoir 12 to the patient. Restrictor 20 comprises a plunger assembly, which is mounted within the housing of controller 10, and an adapter which receives and is subsequently permanently affixed to the tube 14; the adapter thus being a throw-away component. This adapter, which is shown in FIGS. 5–7, is easily engaged in a holder 60 (FIGS. 1 and 4), which also forms part of restrictor 20. Holder 60 is mounted on and extends outwardly from the side of control 10. Thus, rather than having a conventional hinge type door, as has characterized prior art restrictors, the restrictor of the present invention includes a throw-away adapter sub-assembly and a plunger sub-assembly, which is permanently attached to the housing of the controller, into which the adapter and tube may be easily inserted.

Figure 3:
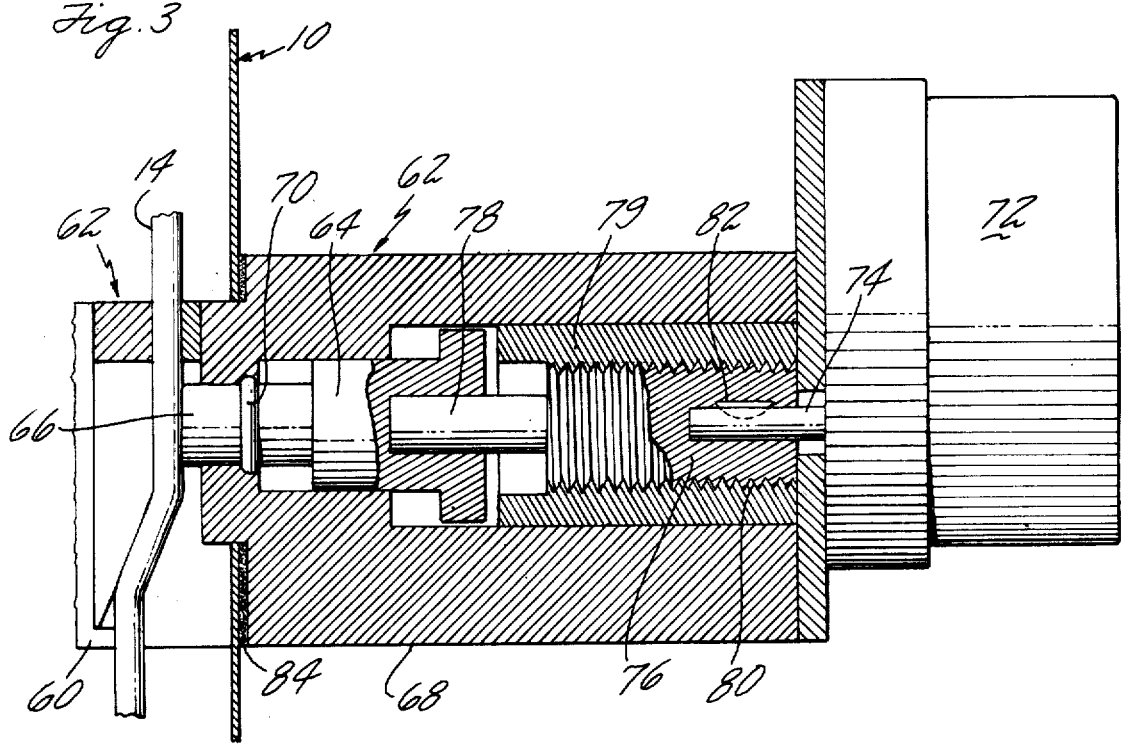
FIG. 3 is a cross-sectional, side elevation view of the restrictor of the system of FIG. 1.
Figure 4:
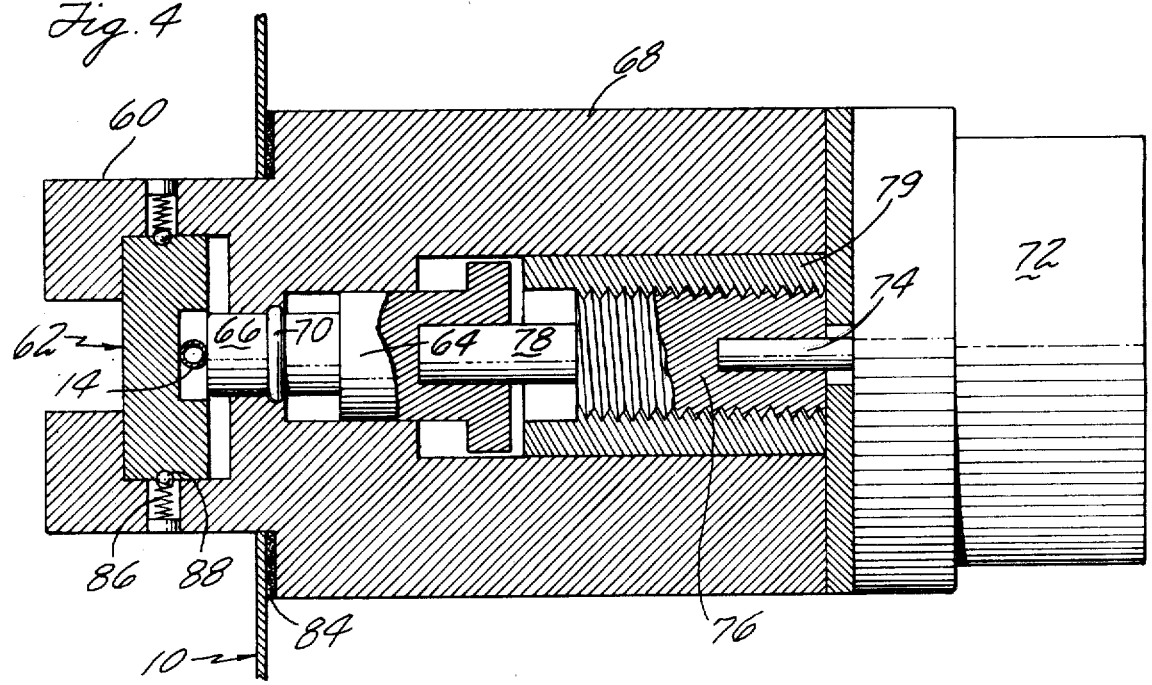
FIG. 4 is a view, taken along line 3—3, of the restrictor of FIG. 3.

Referring now simultaneously to FIGS. 3 and 4, the tube 14 is placed in a channel in the adapter, which is indicated generally at 62, and the adapter is then placed in the holder 60 (not shown in FIG. 3). The foregoing action will place the tube 14 in alignment with the restrictor plunger 64 which, pursuant to the "Set-Up" operational mode described above, will be in the fully withdrawn position; this position being depicted in FIGS. 3 and 4. In this position the end 66 of plunger 64 will be lightly in contact with or very closely spaced from tube 14 but will not be compressing the tube. The plunger 64 will be comprised of a non-conductive plastic material thereby precluding the possibility of electrical current flow between the controller and the fluid flowing in tube 14 in the unlikely event of the tube being punctured by the plunger action.

The plunger 64 is received in a chamber formed in a housing 68. Housing 68 is mounted, in any suitable manner, on the interior of the housing of controller 10 and has an extension which projects outwardly through the wall of the controller as best seen in FIG. 4. This extension defines the holder 60 which receives the adapter 62. The cavity in housing 68 which receives plunger 64 is sized relative to the plunger so as to insure a precise slip fit; the plunger and housing cavity each having three complimentary portions of constant but different diameter in the embodiment shown. The end portion 66 of plunger 64 is provided with a groove which receives an O-ring seal 70. The positioning of the seal receiving groove in plunger 64 and the width of the end wall of housing 68 are selected such that the O-ring will remain in contact with the wall of the housing aperture through which the plunger extends throughout the full excursion of the plunger. The O-ring seal 70 prevents liquid from penetrating into the interior of controller 10 and particularly into the interior of the plunger sub-assembly.

The motion which is imparted to plunger 64 is generated by a motor 72. Motor 72, which is a stepping motor in the disclosed embodiment, receives input signals from driver transistor pairs in the stepping motor controller of FIG. 2. Motor 72, which includes reduction gearing within its case, has a rotatable output shaft 74 which is affixed, for example by keying, to a threaded "bolt" 76. Accordingly, bolt 76 will turn with the motor shaft 74 but is also capable of axial movement relative to the motor shaft. In the disclosed embodiment the plunger 64 is press fit onto an extension 78 of bolt 76 whereby the plunger will move with the bolt. Alternatively, a rotatable joint may be established between plunger 64 and bolt extension 78 whereby the plunger will move axially with the bolt but will not rotate therewith.

The bolt 76 rides in an internally threaded sleeve 79 which is press fit or otherwise secured in the cavity in housing 68 so as to be secured against rotation. In one reduction to practice of the invention, sleeve 79 and bolt 76 were provided with eighty complimentary threads per inch; these threads being indicated at 80. As the motor rotates, accordingly, the bolt will rotate as a result of the coupling of the motor output shaft 74 to bolt 76 as indicated at 82. However, because of the cooperation between the complimentary threads on the bolt and sleeve, the bolt will also move axially and this axial motion will be imparted to plunger 64.

It is, of course, essential that foreign particles and liquids be prevented from contact with the complimentary threads on the bolt 76 and sleeve 79. This is in part accomplished through the use of the aforementioned O-ring seal 70 and also by the insertion of a gasket 84 between the inside surface of the housing of controller 10 and the exterior of plunger housing 68. The two stepped portions of plunger 64, which are of greater diameter than end portion 66, also contribute to elimination of the possibility of foreign matter entering the chamber in which the plunger moves and, if necessary, these two additional portions of plunger 68 may also be provided with O-ring seals.

Referring to FIG. 4, the tube receiving adapter 62 is releasably captured within the holder 60, which as noted is formed as an extension of housing 68, by means of a pair of oppositely disposed spring-loaded latch mechanisms. These latch mechanisms, in the manner well known in the art, each comprise a spring 86 and a ball 88 which engages a detent in the side of the adapter 62. Referring again to FIG. 1, the adapter will be inserted from the top of holder 60 and will be guided into the locked position by means of cooperating angled wall portions on the adapter and holder. The adapter is easily removed from the holder merely by applying upward force to the bottom thereof.

Referring now simultaneously to FIGS. 5-7, the adapter 62 is comprised of two pieces of molded plastic, namely a clamp portion, indicated generally at 90, and a cap portion, indicated generally at 92. Once the cap has been installed on the clamp it may not be removed therefrom.

The clamp portion 90 of the restrictor adapter defines a channel 94. Channel 94 is sized and shaped to receive the tube 14. The channel 94 performs two functions. Firstly, it securely holds the tube in place due to the fact that the width of the channel is slightly less than the "relaxed" shape of the tube. When the tube 14 is placed in the channel 94 it is caused to first follow a generally vertical path and, when it reaches the sloped wall portion indicated at 96 in FIG. 6, the tube is bent toward the left as the apparatus is depicted in FIG. 3. The causing of the tube 14 to deviate from the vertical orientation at a point below where the end 66 of plunger 64 contacts the tube; i.e., below a depressed circular area 98 of clamp portion 90; facilitates the insertion of the adapter into the holder 60. Thus, the second function of channel 94 is to allow the adapter to be lowered into the holder 60 with a clearance for the end 66 of plunger 64. As previously noted, the compressing surface of the plunger is, with the adapter installed in the holder 60, in registration with the depressed circular region 98 of clamp portion 90. Accordingly, the adapter may be lowered into place easily and without interference with the plunger.

Proper positioning of the adapter within the holder 60 is further insured by the placement of the detents 100, which are engaged by the aforementioned spring-loaded latching mechanisms in holder 60, and also by the provision of a pair of outwardly extending flanges 102 on clamp portion 90. The shoulders defined by the lower ends of these flanges 102 of clamp portion 90 will be supported either on the top surface of the holder 60 or on a complimentary internal surface. As also previously mentioned, the adapter, and more precisely the clamp portion 90, is provided with a pair of angled guide surfaces 104 which slide on complimentary surfaces in holder 60.

The clamp portion 90 of adapter 62 is further provided with a pair of blind holes 106. These blind holes, which have the configuration which may best be seen from joint consideration of FIGS. 5 and 6, are sized and shaped to receive prongs 108 which extend outwardly from the cap portion 92 of the adapter. After the tube 14 has been positioned in the channel 94, the cap 92 is snapped into engagement with the clamp 90 thereby permanently locking the tube 14 into the adapter. Assembly of the restrictor is thereafter completed merely by inserting the adapter 62 in the holder 60 and the system is ready for "Set-Up" and use in the manner described above.

While a preferred embodiment has been shown and described, various modifications and substitutions may be made thereto without departing from the spirit and scope of the invention. Accordingly, it is to be understood that the present invention has been described by way of illustration and not limitation.

What is claimed is:

1. A control for regulating the flow of a liquid through a compressible tube, said control operating in cooperation with a drop sensor which provides output signals commensurate with the flow of fluid from a reservoir into the tube, said control comprising:
   restrictor means for applying a variable compressive force to a tube through which the flow is to be regulated, said restrictor means including:
   adapter means, said adapter means having a first passage extending therethrough, said first passage being sized and shaped to receive the tube, said adapter means further defining a second passage which is transverse to and intersects said first passage, said second passage extending from a first side of said adapter means to said first passage;

plunger means, said plunger means having a housing which defines an internal chamber, said plunger means including a plunger movable longitudinally within said chamber, said plunger having a portion which extends outwardly through the first wall of said housing, said housing further defining a holder on the exterior of said first wall, said holder receiving and supporting said adapter means with said first side of said adapter means facing said first wall of said plunger means housing and with said plunger in registration with said adapter means second passage;

motor means, said motor means having a rotatable output shaft; and means coupling said motor means output shaft to said plunger means plunger, said coupling means extending into said plunger means housing defined chamber and converting the motor means output shaft rotory motion to longitudinal motion of said plunger;

computer means, said computer means including a program memory and a scratchpad memory, said computer means having a stored program comprising instructions for producing output signals commensurate with flow rate errors and volume yet to be delivered through the tube;

keyboard means for generating command signals and data signals commensurate with a desired flow rate and quantity, said keyboard means being connected to said computer means whereby the generated command and data signals may be supplied to said computer means;

means delivering the drop sensor output signals to said computer means whereby said computer means may compare actual and desired flow rates and generate first error signals as a result of said comparison and whereby said computer means may determine the volume of fluid delivered through the tube and compare the delivered volume with the desired volume and generate second error signals when the total desired volume has been delivered through the tube; and means applying said computer means generated error signals to said restrictor means motor means whereby the tube will be compressed to a degree commensurate with the desired flow rate in response to the said first error signals and will be compressed to a point where flow is prevented in response to the said second error signals.

2. The apparatus of claim 1 further comprising:
display means coupled to said computer means, said display means providing a visual presentation of data entered from said keyboard means, said display means further providing a display of the volume yet to be delivered during periods when there is flow through the tube.

3. The apparatus of claim 2 further comprising:
alarm means for generating warning signals, said alarm means being connected to said computer means and being responsive to energizing signals generated by said computer means, said computer means being programmed to generate said energizing signals when the actual flow rate deviates from the desired value and is not returned to the desired value in response to the said first error signals within a predetermined time.

4. The apparatus of claim 3 wherein said alarm means is also energized when the volume yet to be infused reaches zero.

5. The apparatus of claim 3 wherein said keyboard means includes a key which will command the full retraction of said plunger means plunger, said computer means generating a first error signal which will drive said motor means output shaft to a first limit of motion in response to operation of said full retraction command key.

6. The apparatus of claim 1 wherein said adapter means comprises:
a clamp member, said clamp member being provided with a tube receiving recess extending between oppositely disposed second and third sides thereof; and
a cap member, said cap member being engagable with said clamp member to capture the tube in said recess.

7. The apparatus of claim 6 wherein said clamp member tube receiving recess comprises:
a first portion extending inwardly from said second side and having a width substantially equal to the tube diameter, a second intermediate portion having a cross-section which is larger than the tube diameter, said second portion having a flat base which is in registration with and transverse to the axis of said second passage, and a third portion which extends from said second portion to said third side, said third portion having an axis which is angularly inclined with respect to the axis of said first portion in a direction which is away from said adapter means first side.

8. The apparatus of claim 7 wherein said cap member includes a plurality of irregularly shaped projections and wherein said clamp member further includes latch means for permanently engaging said projections whereby said adapter means will be irremovably installed on a tube by insertion of the tube in said recess portions followed by engagement of said cap member extensions with said clamp member latch means.

9. The apparatus of claim 1 wherein said coupling means comprises:
an externally threaded elongated bolt means positioned in said chamber, said bolt means having an axis and being sized for axial movement within said chamber;
an internally threaded sleeve afixed to the interior of said chamber, the threads on said sleeve being complementary to and engaging the thread on said bolt means; and
means establishing a driving connection between said motor means output shaft and said bolt means, said driving connection establishing means extending into said chamber and engaging said bolt means, said driving connection establishing means imparting rotation to said bolt means and permitting said bolt means to move axially relative to said driving connection establishing means during the rotation thereof.

10. The apparatus of claim 1 further comprising:
display means coupled to said computer means, said display means providing a visual presentation of data entered from said keyboard means, said display means further providing a display of the volume yet to be delivered during periods when there is flow through the tube.

11. The apparatus of claim 10 further comprising:

alarm means for generating warning signals, said alarm means being connected to said computer means and being responsive to energizing signals generated by said computer means, said computer means being programmed to generate said energizing signals when the actual flow rate deviates from the desired value and is not returned to the desired value in response to the said first error signals within a predetermined time.

12. The apparatus of claim 11 wherein said coupling means comprises:
an externally threaded elongated bolt means positioned in said chamber, said bolt means having an axis and being sized for axial movement within said chamber;
an internally threaded sleeve afixed to the interior of said chamber, the threads on said sleeve being complementary to and engaging the thread on said bolt means; and
means establishing a driving connection between said motor means output shaft and said bolt means, said driving connection establishing means extending into said chamber and engaging said bolt means, said driving connection establishing means imparting rotation to said bolt means and permitting said bolt means to move axially relative to said driving connection establishing means during the rotation thereof.

13. The apparatus of claim 12 wherein said adapter means comprises:
a clamp member, said clamp member being provided with a tube receiving recess extending between oppositely disposed second and third sides thereof; and
a cap member, said cap member being engagable with said clamp member to capture the tube in said recess.

14. The apparatus of claim 13 wherein said clamp member tube receiving recess comprises:
a first portion extending inwardly from said second side and having a width substantially equal to the tube diameter, a second intermediate portion having a cross-section which is larger than the tube diameter, said second portion having a flat base which is in registration with and transverse to the axis of said second passage, and a third portion which extends from said second portion to said third side, said third portion having an axis which is angularly inclined with respect to the axis of said first portion in a direction which is away from said adapter means first side.

15. The apparatus of claim 14 wherein said cap member includes a plurality of irregularly shaped projections and wherein said clamp member further includes latch means for permanently engaging said projections whereby said adapter means will be irremovably installed on a tube by insertion of the tube in said recess portions followed by engagement of said cap member extensions with said clamp member latch means.

16. The apparatus of claim 6 wherein said clamp member tube receiving recess comprises:
a first portion extending inwardly from said second side and having a width substantially equal to the tube diameter, a second intermediate portion having a cross-section which is larger than the tube diameter, said second portion having a flat base which is in registration with and transverse to the axis of said second passage, and a third portion which extends from said second portion to said third side, said third portion having an axis which is angularly inclined with respect to the axis of said first portion in a direction which is away from said adapter means first side.

17. The apparatus of claim 16 wherein said cap member includes a plurality of irregularly shaped projections and wherein said clamp member further includes latch means for permanently engaging said projections whereby said adapter means will be irremovably installed on a tube by insertion of the tube in said recess portions followed by engagement of said cap member extensions with said clamp member latch means.

18. The apparatus of claim 1 wherein said restrictor means actuator comprises:
a housing, said housing defining a cylinder having an axis;
a piston positioned for movement in said cylinder;
an extension of said piston, said piston extension projecting through a wall of said housing at a point in alignment with the compressible tube whereby said piston rod may be extended from or retracted into said housing;
motor means, said motor means having a rotatable output shaft; and
means coupling said motor means output shaft to said piston, said coupling means extending into said cylinder and converting the rotary motor output shaft motion to axial motion of said piston.

19. The apparatus of claim 18 wherein said coupling means comprises:
an externally threaded elongated bolt means positioned in said cylinder, said bolt means having an axis and being sized for axial movement within said cylinder;
an internally threaded sleeve afixed to the interior of said cylinder, the threads on said sleeve being complementary to and engaging the thread on said bolt means;
means establishing a driving connection between said motor means output shaft and said bolt means, said driving connection establishing means extending into said cylinder and engaging said bolt means, said driving connection establishing means imparting rotation to said bolt means and permitting said bolt means to move axially relative to said driving connection establishing means during the rotation thereof; and
means connecting said bolt means to said piston.

20. In a device for controllably compressing a flexible tube to vary the flow therethrough, the device including a reciprocal plunger which exerts force on the tube, the device having a housing with an aperture through which the plunger extends, the improvement comprising:
holder means, said holder means being mounted on the device housing;
a clamp member, said clamp member being provided with a tube receiving recess extending between oppositely disposed second and third sides thereof; and
a cap member, said cap member being engagable with said clamp member to capture the tube in said recess, said cap and clamp members cooperating to define a discardable adapter which is received in said holder means.

21. The apparatus of claim 20 wherein said clamp member tube receiving recess comprises:

a first portion extending inwardly from said second side and having a width substantially equal to the tube diameter, a second intermediate portion having a cross-section which is larger than the tube diameter, said second portion having a flat base which is in registration with and transverse to the axis of the reciprocal plunger, and a third portion which extends from said second portion to said third side, said third portion being angularly inclined with respect to said second portion flat base in a direction which is away from said housing means.

22. The apparatus of claim 21 wherein said cap member includes a plurality of irregularly shaped projections and wherein said clamp member further includes latch means permanently engaging said projections whereby said clamp and cap members define adapter means which will be pemanently installed on a tube by insertion of the tube in said recess portions followed by engagement of said cap member extensions with said clamp member latch means.

* * * * *